United States Patent [19]

Millay

[11] Patent Number: 5,271,409
[45] Date of Patent: Dec. 21, 1993

[54] NON-BUNCHING CINCH RING ENGAGEMENT FOR BLOOD PRESSURE CUFF

[75] Inventor: Jack M. Millay, Beaverton, Oreg.

[73] Assignee: SpaceLabs Medical, Inc., Redmond, Wash.

[21] Appl. No.: 791,573

[22] Filed: Nov. 12, 1991

[51] Int. Cl.⁵ .............................................. A61B 5/00
[52] U.S. Cl. ...................................... 128/686; 606/202
[58] Field of Search .............................. 128/680–686, 128/327; 24/197–200, 265 BC; 606/202, 203

[56] References Cited

U.S. PATENT DOCUMENTS

| | | |
|---|---|---|
| 2,156,870 | 5/1939 | Rineer et al. . |
| 2,480,430 | 8/1949 | Walters . |
| 2,713,708 | 7/1955 | Anderson . |
| 3,005,454 | 10/1961 | Bird . |
| 3,450,136 | 6/1969 | Anderson . |
| 3,633,567 | 1/1972 | Sarnoff . |
| 4,300,573 | 11/1981 | Rebbe et al. . |
| 4,429,699 | 2/1984 | Hatschek . |
| 4,832,040 | 5/1989 | Ruff . |
| 4,838,276 | 6/1989 | Nagai et al. ............... 128/686 |

FOREIGN PATENT DOCUMENTS

WO83/00426  2/1983  PCT Int'l Appl. .

*Primary Examiner*—Lee S. Cohen
*Assistant Examiner*—Robert L. Nassor, Jr.
*Attorney, Agent, or Firm*—Seed and Berry

[57] ABSTRACT

A blood pressure cuff assembly that can be self-applied. The fixed end of the cuff assembly captures a cinch ring. Lateral stiffness is imparted to the fixed end to prevent it from bunching on the cinch ring. The stiffness may be imparted by the material of the fixed end or a separate stiff member may be added to the fixed end. An interface piece may be employed to connect the fixed end to the cinch ring. Stiffness is imparted to the interface piece, the fixed end, or both.

8 Claims, 3 Drawing Sheets

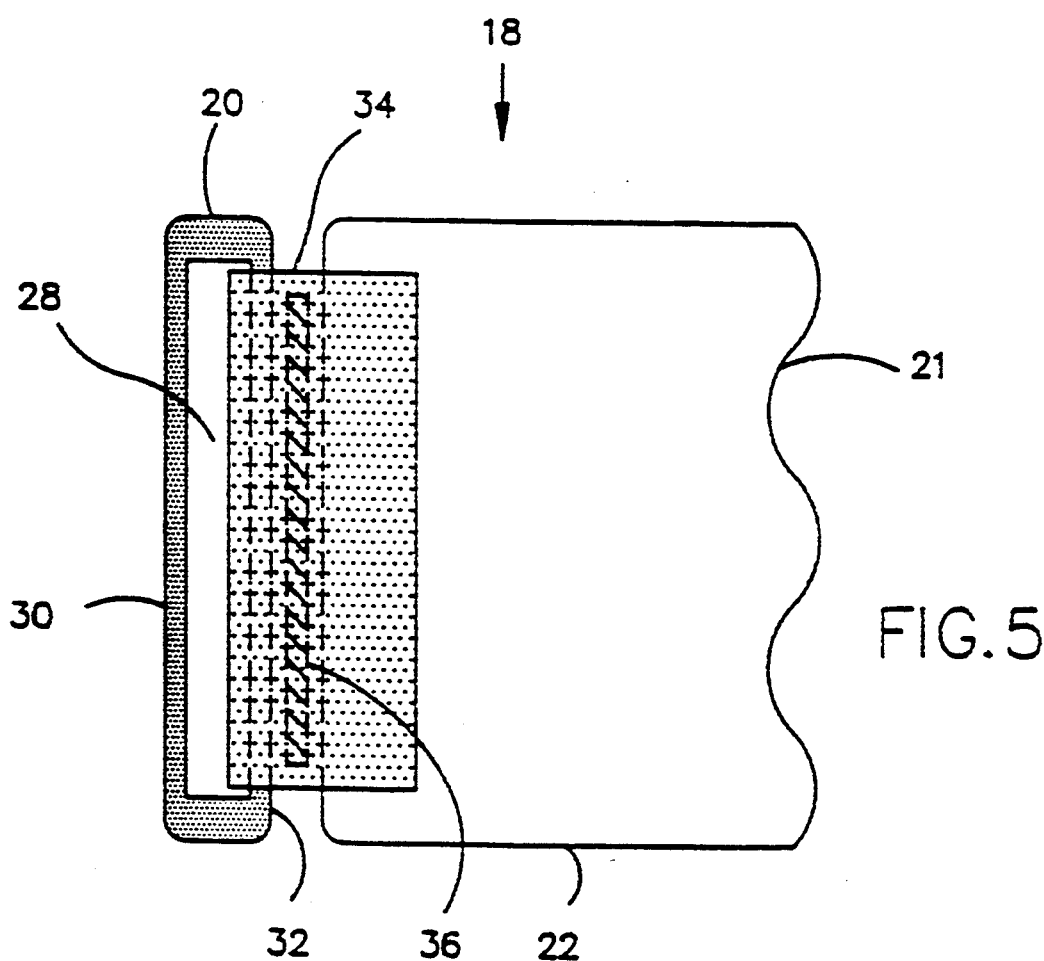

NON-BUNCHING CINCH RING ENGAGEMENT FOR BLOOD PRESSURE CUFF

TECHNICAL FIELD

The present invention relates to blood pressure cuffs used for taking blood pressure measurements, and more particularly, to self-applied cuffs that are placed around the arms of patients.

BACKGROUND OF THE INVENTION

Blood pressure cuffs are well known in the prior art and comprise an elongated, flexible band having a predetermined length and width, a body side face and an outward face. The front and back faces of the band are joined together around their peripheries to form an inflatable bladder. A hose portion coupled to the bladder and usually integrally formed therewith extends out from the band through an opening in the periphery.

The band is adapted to be wrapped around a limb, such as an arm or leg, to measure blood pressure. Attachment means such as VELCRO TM is provided with the band to hold the band on the limb. Some self-applied cuffs include a buckle in the form of an elongated cinch ring to which one end of the band is attached and through which the other, or free, end of the band is passed to form a sleeve.

When wrapping the band around the arm, it is desirable for accuracy of measurement that the center of the bladder be located over the brachial artery on the inner side of the upper arm. It has been found most convenient in ambulatory measurement applications when wrapping the band around the arm that the hose portion extend through a top periphery or edge of the cuff such that a hose coupled between the cuff and monitoring device is then routed up the front of the arm across the back of the neck to the other side of the body to the monitoring device, which is usually strapped to the patient's waist. In order to accomplish this, the slot in the periphery of the cuff is offset from the center of the bladder so that the hose portion of the bladder extends along the front of the arm.

When applying a self-applied cuff to an arm of a patient, e.g., the left arm, it has been found most convenient to insert the free end of the cuff through the buckle of the cuff at the opposite end with the fastener material on one face of the cuff facing out. This forms a sleeve into which the arm is inserted. To tighten the cuff, the user reaches under his arm and pulls the free end of the cuff away from the body trunk. Then the cuff is pulled over the buckle toward the trunk and the loop and hook fastener material is pressed together. If the free end of the cuff is not pulled away at precisely the proper angle with respect to the cinch ring, the cinch ring tends to cock with respect to the length of the cuff. As a result, the cuff bunches up at one end or the other of the elongated cinch ring. This makes fitting and adjusting the cuff less convenient and more difficult for the user. It may also result in the cuff being too loose if it bunches too severely on the cinch ring.

It is desirable, therefore, to provide a cinch ring/cuff arrangement that can be used with a self-applied cuff design to overcome the tendency of the cuff to bunch up in the cinch ring.

U.S. Pat. No. 4,832,040 solves the issue of a cinch ring sliding out of the proper position in relation to the cuff by providing the ring with projections which are captured by stitches in the cuff to secure the cinch ring in the position on the cuff. This invention uses an ordinary cinch ring, but modifies the attachment to the cuff in order to accomplish the same end result.

SUMMARY OF THE INVENTION

The present invention relates to a self-applied blood pressure cuff adapted for use on an arm of the body. It comprises a band having a cinch ring end and a free end, a body side face and an outward face, and a compartment. The cinch ring is held in place at the cinch ring end by a loop of the cuff band that passes through the cinch ring. The length of the cinch ring exceeds the width of the cuff band so that the cinch ring freely rotates about the loop of the cinch ring end. The length of the cinch ring also exceeds the width of the free end. The compartment may act as an inflatable bladder or a separate inflatable bladder may be inserted into the compartment. The bladder includes a portion which protrudes from the compartment.

In each of the embodiments of the invention, transverse stiffness is imparted to the cuff band at or near the coupling to the cinch ring. This stiffness prevents the cuff band from bunching up on the cinch ring without the need for a special cinch ring. In the preferred embodiments, an interface piece is employed to couple the cinch ring to the cuff band. The stiffness may be imparted to the interface piece and/or cuff band by using stiff materials to make the interface piece and/or cuff band. Alternatively, stiff members may be affixed into or onto the interface piece and/or cuff band. The stiffness is preferably imparted substantially only transverse to the elongation of the band so as not to prevent the band from being comfortably wrapped around the arm of the patient.

BRIEF DESCRIPTION OF THE DRAWINGS

FIG. 5 is a plan view of a third embodiment of the cinch ring/cuff assembly of the present invention.

DETAILED DESCRIPTION OF THE INVENTION

Figure 1:
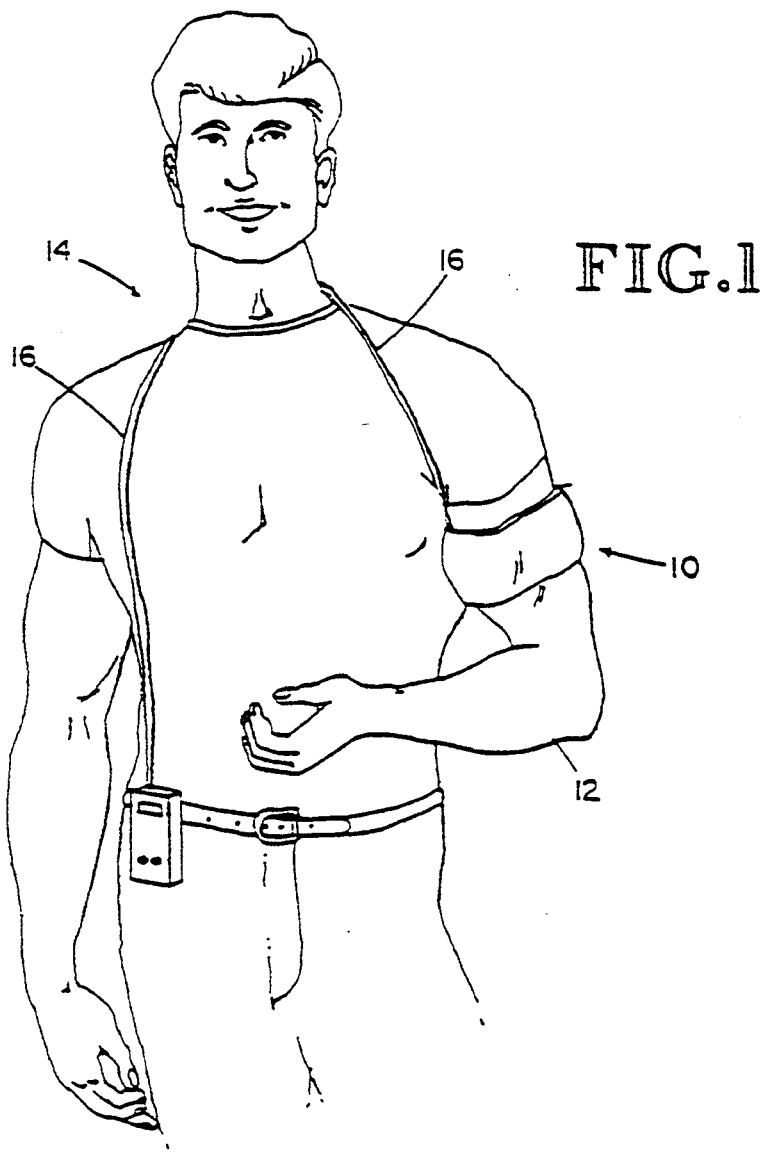
FIG. 1 is a diagram showing a self-applied blood pressure cuff assembly in use.

A diagram showing a self-applied blood pressure cuff assembly in use is shown in FIG. 1. Blood pressure cuff assembly 10 can, for example, be applied to the upper portion of the left arm 12 of a right-handed person 14. The blood pressure cuff assembly 10 contains a bladder (not shown) that can be inflated and deflated through the application of air pressure through hose 16 that is connected to the bladder of the blood pressure cuff assembly. The bladder and hose can be made from a rubber material. In one application, the self-applied blood pressure cuff assembly 10 can be attached through hose 16 to a portable unit that periodically inflates the blood pressure cuff assembly, reads the systolic and diastolic pressures of the person 14, and records the blood pressure data for later retrieval.

The blood pressure cuff assembly 10 includes an elongated band 22. The band has two faces, a body side face and an outward face. When the cuff assembly is in use, the body side face of the band 22 is adjacent the skin of the person 14, while the outward face is directed away from the person's arm. The body side face and outward face, when sewn together, form the elongated band 22 that forms the outside of the blood pressure cuff assembly 10. Between the faces a compartment is formed which contains the bladder. The blood pressure cuff assembly can be used on a person's right arm by inverting the bladder within the blood pressure assembly 10 about an axis lying in the elongated direction of the blood pressure cuff assembly.

Figure 2:
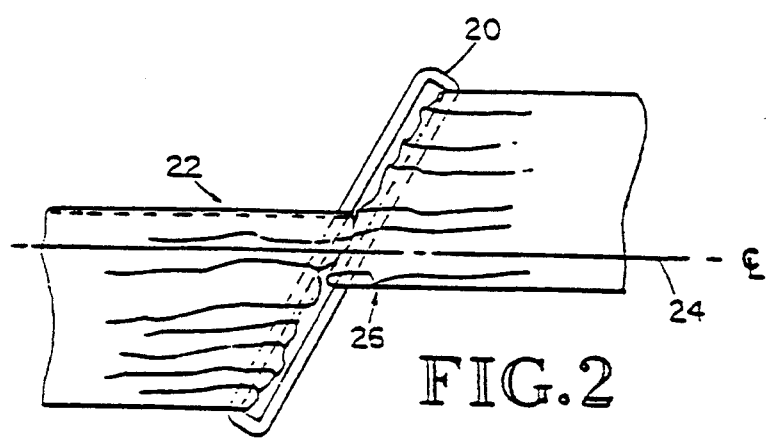
FIG. 2 is a closeup plan view showing the "bunching-up" problem of the prior art.

FIG. 2 is a closeup plan view showing the bunching up problem of self-applied blood pressure cuff assemblies of the prior art. Cinch ring 20, attached to fixed end 22 of the blood pressure cuff assembly 10 can become non-perpendicular to the longitudinal axis 24 of the blood pressure cuff assembly 10 when the cuff assembly is being applied to a person's arm. Thus, that portion of the flexible band which comprises the fixed end 22 gathers toward one end of elongated cinch ring 20. Accordingly, the portion of the free end 26 that is passing through the cinch ring 20 tends to gather toward the other end of the elongated cinch ring 20. As the material of both ends of the flexible band continues to concentrate at the respective ends of the cinch ring 20, the cinch ring 20 becomes twisted (at an angle of up to 45 degrees) with respect to the length of the person's arm. Subsequently, when the cuff assembly 10 is inflated, the bunched-up cuff material and the cinch ring 20 itself can pinch and possibly bruise the person's arm.

Figure 3:
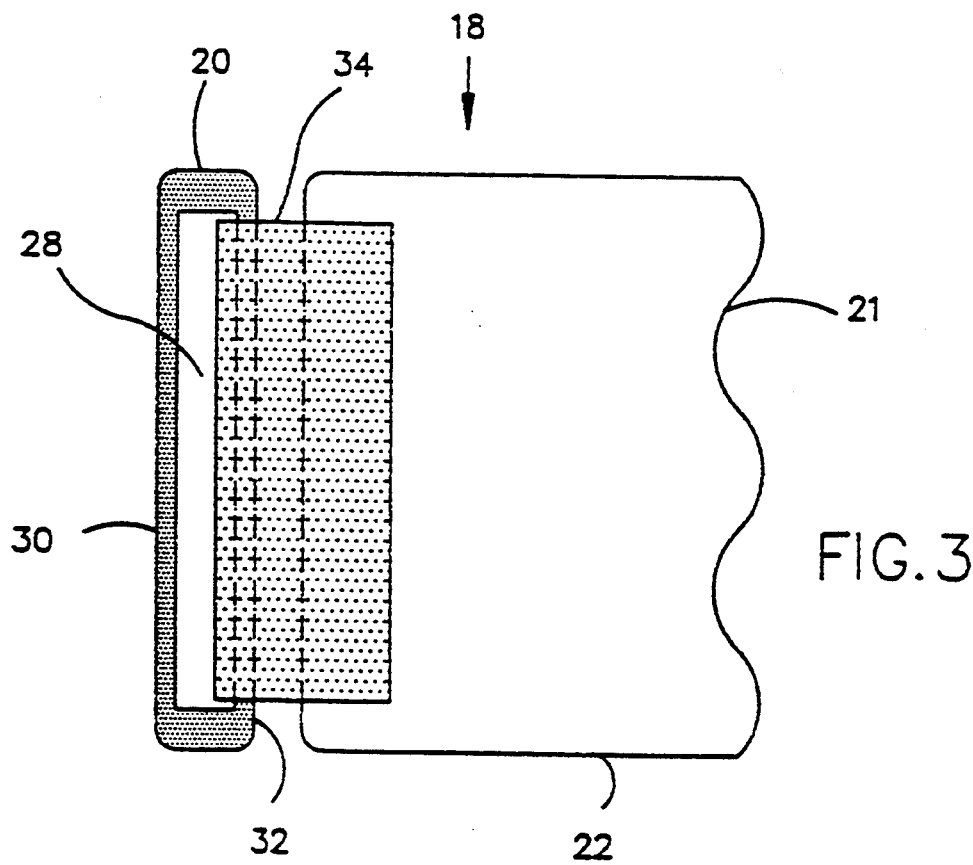
FIG. 3 is a plan view of one embodiment of the cinch ring/cuff assembly of the present invention.

FIG. 3 is a plan view of a first embodiment of the cinch ring/band assembly 18. In this embodiment, cinch ring 20 comprises an elongated ring with a slot 28. The cinch ring 20 also comprises two parallel edges, outer edge 30 and inner edge 32. Inner edge 32 is captured by a stiff, non-bunching interface piece 34. The end of the interface piece 34 opposite to the cinch ring 20 is affixed to the fixed end 22 of the band 21. The stiffness of interface piece 34 prevents it from bunching up within the cinch ring slot 28. Since the interface piece 34 is affixed to the band 21, band 21 is likewise prevented from bunching. Interface piece 34 may be made from any stiff material, such as metal or plastic.

Figure 4:
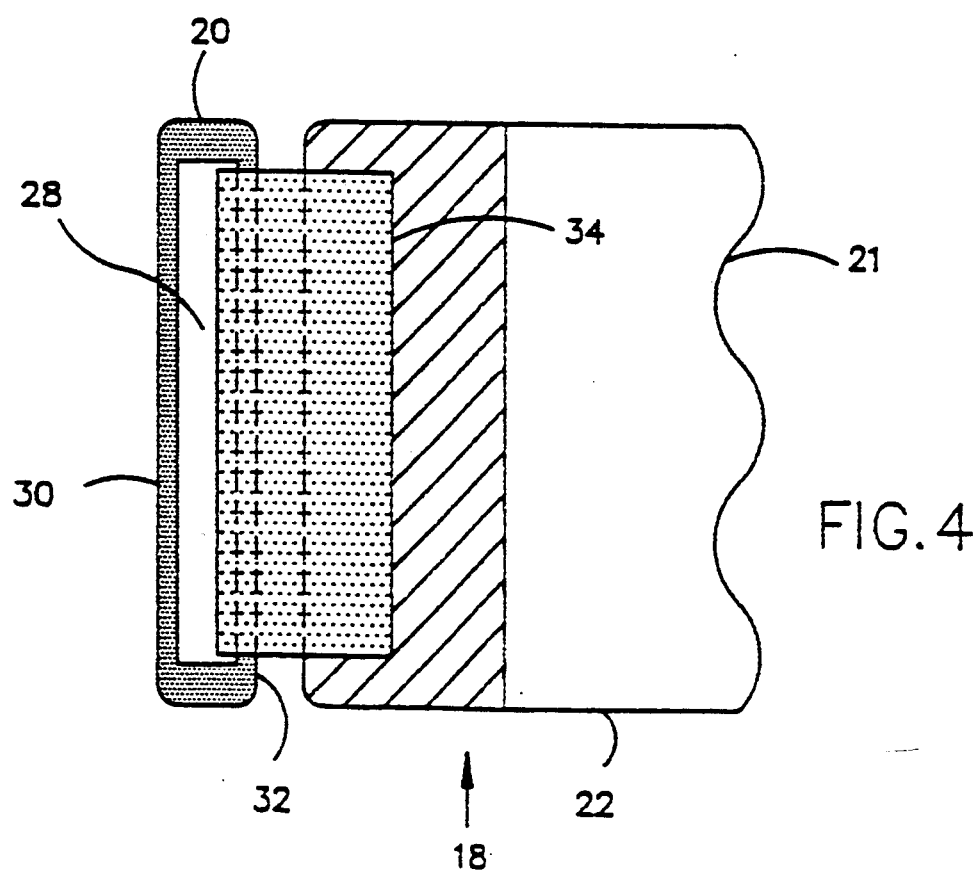
FIG. 4 is a plan view of a second embodiment of the cinch ring/cuff assembly of the present invention.

FIG. 4 shows a plan view of a second embodiment of the cinch ring/band assembly 18. In this embodiment, the fixed end 22 of the band 21 is stiffened, such as by the addition of a curing resin. However, the remainder of the band 21 is flexible enough to allow the bladder to expand. In the embodiment of FIG. 4, the interface piece 34 coupling to the band 21 to the cinch ring 20 may be stiff or flexible since the transverse stiffness is provided by an integrally formed stiff portion of the band 21. As long as the portion of the interface piece 34 that is not affixed to the band is kept to a minimum, the stiffness of the band 21 will prevent more than a minimal amount of bunching by the interface piece 34 within the cinch ring 20. The portion of the interface piece 34 not affixed to the band 22 need only be broad enough to couple to the cinch ring 20.

A third embodiment of the invention is depicted in FIG. 5. A stiff member 36 is affixed to or embedded in the interface piece 34. This may be accomplished by various methods, such as by creating a transverse compartment within the interface piece 34 and inserting a metal or stiff plastic bar in the compartment. This allows the interface piece 34 and the band 21 to be made of flexible material, while retaining the stiffness necessary to prevent bunching. Again, for optimum anti-bunching effect, the portion of the interface material not immediately adjacent the stiff member 36 should be kept to a minimum. The portion not immediately adjacent the stiff member 36 need only be broad enough to be reliably coupled to the band 21 and cinch ring 20. This embodiment may be most useful in converting prior art cuff assemblies into those of the present invention merely by affixing a stiff bar to the interface piece 34 or fixed end 22.

In each of the embodiments the interface piece 34 need not be separable from the band 21. A single piece construction could be adopted as long as stiffness is imparted to the band transverse to the elongation of the band. The stiffness should be either part of the coupling to the cinch ring 20 or as close as possible to the cinch ring 20.

While those skilled in the art will readily appreciate that modifications of the embodiments of the present invention described above may be made, the spirit and scope of the present invention is limited only by the following claims.

I claim:

1. A blood pressure cuff assembly, comprising:
   an elongated band having first and second ends, a body side face, an outward face, and an internal bladder;
   a cinch ring having an inner edge and an outer edge; and
   an interface piece formed at the first end of the elongated band, the interface piece capturing the inner edge of the cinch ring, the interface piece being relatively stiff as compared to the remainder of the band to restrict transverse movement of interface piece relative to the cinch ring, the interface piece being relatively stiff independent of any stiffness imparted by the cinch ring;
   wherein the interface piece includes a web of flexible material extending between the first end of the elongated band and the cinch ring to secure the cinch ring to the elongated band, and a rigid stiffening member secured to said web between the end of the elongated band and the cinch ring, the stiffening member having a longitudinal axis extending transverse to the elongation of the band and parallel to the cinch ring edge.

2. The blood pressure cuff assembly of claim 1 wherein the interface piece is substantially composed of plastic.

3. A blood pressure cuff assembly, comprising:
   an elongated band having first and second ends, a body side face, an outward face, and an internal bladder;
   a cinch ring having an inner edge and an outer edge; and
   an interface piece formed at the first end of the elongated band, the interface piece capturing the inner edge of the cinch ring, the interface piece being relatively stiff as compared to the remainder of the band to restrict transverse movement of interface piece relative to the cinch ring, the interface piece being relatively stiff independent of any stiffness imparted by the cinch ring;
   wherein the interface piece is integrally formed by a portion of the first end of the elongated band that is composed of a material that is relatively stiff, in a direction transverse to the elongation of the elongated band, compared to the remainder of the elongated band to restrict transverse movement of the interface piece relative to the cinch ring, the material being relatively stiff independent of any stiffness imparted by any portion of the interface piece being of double thickness to capture the cinch ring.

4. A blood pressure cuff assembly, comprising:

an elongated band having first and second ends, a body side face, an outward face, and an internal bladder;

a cinch ring having an inner edge and an outer edge; and an interface piece formed at the first end of the elongated band, the interface piece capturing the inner edge of the cinch ring, the interface piece being relatively stiff as compared to the remainder of the band to restrict transverse movement of interface piece relative to the cinch ring, the interface piece being relatively stiff independent of any stiffness imparted by the cinch ring;

wherein the interface piece incudes a web of material extending between the first end of the elongated band and the cinch ring to secure the cinch ring to the elongated band, the material being relatively stiff, in a direction transverse to the elongation of the elongated band, compared to the stiffness of the elongated band, the material being relatively stiff independent of any stiffness imparted by any portion of the interface piece being of double thickness to capture the cinch ring.

5. The blood pressure cuff assembly of claim 4 wherein a portion of the interface piece is integral to the first end of the band, the integral portion being relatively stiff compared to the remainder of the band, the interface piece also including a web of material extending between the integral portion of the interface piece and the cinch ring to secure the cinch ring to the band.

6. A method of restricting bunching of a fixed end of an elongated band secured to a cinch ring that extends transverse to the elongation of the elongated band, the method comprising stiffening the elongated band at the fixed end thereby to prevent the fixed end of the elongated band from bunching where it is secured to the cinch ring, the stiffening step being independent of any stiffening imparted by the cinch ring wherein the stiffening step includes making the fixed end of the elongated band of a relatively stiff material compared to the remainder of the elongated band, the material being relatively stiff in a direction transverse to the elongation of the elongated band independent of any stiffness imparted by any portion of the fixed end being of double thickness to capture the cinch ring.

7. The method of claim 6 wherein the stiffening step includes joining the cinch ring to the fixed end of the elongated band by a web of material that is relatively stiff compared to the stiffness of the elongated band, the material being relatively stiff in a direction transverse to the elongation of the elongated band independent of any stiffness imparted by any portion of the web being of double thickness to capture the cinch ring.

8. A method of restricting bunching of a fixed end of an elongated band secured to a cinch ring having edges that extend transverse to the elongation of the elongated band, the method comprising stiffening the elongated band at the fixed end thereby to prevent the fixed end of the elongated band from bunching where it is secured to the cinch ring, the stiffening step being independent of any stiffening imparted by the cinch ring;

wherein the stiffening step includes joining the cinch ring to the fixed end of the elongated band by a web of material and stiffening the web in a direction extending transverse to the elongation of the band and parallel to said cinch ring edge.

* * * * *

UNITED STATES PATENT AND TRADEMARK OFFICE
CERTIFICATE OF CORRECTION

PATENT NO. : 5,271,409

DATED : December 21, 1993

INVENTOR(S) : Jack M. Millay

It is certified that error appears in the above-identified patent and that said Letters Patent is hereby corrected as shown below:

In column 4, claim 1, line 45, please delete "edge" and substitute therefor --edges--.

In column 6, claim 8, line 36, please delete "edge" and substitute therefor --edges--.

Signed and Sealed this

Fifth Day of July, 1994

Attest:

BRUCE LEHMAN

Attesting Officer     Commissioner of Patents and Trademarks